(12) United States Patent
Park et al.

(10) Patent No.: US 9,741,552 B2
(45) Date of Patent: Aug. 22, 2017

(54) TRIPLE QUADRUPOLE MASS SPECTROMETRY COUPLED TO TRAPPED ION MOBILITY SEPARATION

(71) Applicant: Bruker Daltonics, Inc., Billerica, MA (US)

(72) Inventors: Melvin Andrew Park, Billerica, MA (US); Mark Ridgeway, Arlington, MA (US); Desmond Allen Kaplan, Tewksbury, MA (US); Felician Muntean, Andover, MA (US)

( * ) Notice: Subject to any disclaimer, the term of this patent is extended or adjusted under 35 U.S.C. 154(b) by 26 days.

(21) Appl. No.: 14/978,508

(22) Filed: Dec. 22, 2015

(65) Prior Publication Data

US 2017/0178887 A1    Jun. 22, 2017

(51) Int. Cl.
*H01J 49/42* (2006.01)
*H01J 49/10* (2006.01)

(52) U.S. Cl.
CPC .......... *H01J 49/4225* (2013.01); *H01J 49/10* (2013.01)

(58) Field of Classification Search
CPC .... H01J 49/004; H01J 49/0045; H01J 49/005; H01J 49/0027; H01J 49/0031; H01J 49/10; H01J 49/4225
See application file for complete search history.

(56) References Cited

U.S. PATENT DOCUMENTS

| 7,838,826 B1 * | 11/2010 | Park | G01N 27/622 250/281 |
| 2009/0194688 A1 * | 8/2009 | Bateman | H01J 49/4215 250/292 |
| 2012/0273670 A1 * | 11/2012 | Park | G01N 27/626 250/282 |
| 2012/0286156 A1 | 11/2012 | Park | |
| 2015/0219598 A1 * | 8/2015 | Mordehai | G01N 27/622 250/282 |
| 2016/0118235 A1 * | 4/2016 | Fujita | H01J 49/0031 250/290 |

OTHER PUBLICATIONS

Michelmann Karsten et al., "Fundementals of Trapped Ion Mobility Spectrometry", Journal of the American Society for Mass Spectrometry, Elsevier Science Inc, US, vol. 26, No. 1, Oct. 21, 2014, pp. 14-24.

* cited by examiner

*Primary Examiner* — David E Smith
(74) *Attorney, Agent, or Firm* — Benoît & Côté Inc.

(57) ABSTRACT

The invention provides a method for acquiring fragment ion spectra of substances in complex substance mixtures wherein a trapped ion mobility spectrometer ("TIMS") is used as the ion mobility separation device coupled to a triple quadrupole mass filter assembly. The fragment ion spectra may be used for the identification of high numbers of proteins in complex mixtures, or for a safe quantification of some substances, by their fragment ion mass spectra in a mass spectrometer with upstream substance separator. TIMS, in particular equipped with parallel accumulation, provides the unique possibility to prolong the ion accumulation duration to find more detectable ion species without decreasing the measuring capacity for fragment ion mass spectra. The high measurement capacity for fragment ion mass spectra permits the repeated measurement of low abundance ion species such as to improve the quality of the fragment ion spectra.

20 Claims, 5 Drawing Sheets

TRIPLE QUADRUPOLE MASS SPECTROMETRY COUPLED TO TRAPPED ION MOBILITY SEPARATION

BACKGROUND OF THE INVENTION

Field of the Invention

The invention relates to instruments and methods for the highly efficient acquisition of high numbers of substance-characteristic fragment ion species derived from precursor ions that have been separated by their mobility, in particular to quantify substances with accurate identity and improved signal-to-noise ratio.

Description of the Related Art

In protein science, there is an increasing interest in the quantification of peptides and proteins of a proteolytic digest of proteins extracted from a biological sample, performed by liquid-chromatography/mass-spectrometry (LC-MS). Special attention is directed also to the quantitative analysis of pharmaceutical drugs and their metabolites in pre-clinical studies. Furthermore, complex food/fruit/vegetable matrices may be tested for pesticides and other contaminants. Liquid chromatography coupled to triple quadrupole mass spectrometers renders low-price instrumentation known to be able to detect and to quantify substances with highest sensitivity, but the measurement methods are limited to a few substances appearing in an LC peak of limited duration. Unfortunately, increasing the number of substances by MRM (multiple reaction monitoring) decreases the measurement precision because lesser ions will be measured. In pre-clinical pharmaceutical studies, dozens of triple quadrupole instruments are operated in parallel to analyze hundreds and thousands of samples simultaneously.

U.S. Pat. No. 6,960,761 B2 ("Instrument for Separating Ions in Time as Functions of Preselected Ion Mobility and Ion Mass", D. E. Clemmer, 2001) presents the application of one or more ion mobility separators in combination with mass filters and high-resolution mass analyzers. This document describes a large variety of methods to separate ions in mixtures using a number of different combinations of ion sources, ion traps, ion mobility separators, mass filters, collision cells, ion reactors, and high resolution mass analyzers. Furthermore, correspondent apparatuses are described as being composed of ion sources, ion traps, ion mobility separators, mass filters, collision cells, ion reactors, and high resolution mass analyzers in varying sequence. The high-resolution mass analyzer at the end of the method or device, either a time-of-flight (TOF) or an ion cyclotron resonance (ICR) mass spectrometer, measures the mass spectrum of the fragmented or unfragmented ions with high mass measurement precision. The time-of-flight mass analyzer (TOF) has the advantage of high speed measurements. The high-resolution mass analyzer, however, makes the whole instrument itself as well as its operation expensive. The relatively large physical size of the drift tube used by D. Clemmer in this device, orthogonal to the flight tube of the TOF-MS, makes it less feasible compared with the more compact footprint of modern mass spectrometers.

In U.S. Pat. No. 6,630,662 B1 (A. V. Loboda; 2002: "Setup for Mobility Separation of Ions Implementing an Ion Guide with an Axial Field and Counterflow of Gas") an ion mobility separation device is described, mainly using a constant electric field and a profiled counterflow of gas. The device serves on one hand to collect ions from the ion pulses of a discontinuous MALDI ion source, and on the other hand, to separate the collected ions by their ion mobility. MALDI (matrix assisted laser desorption and ionization) mainly delivers singly charged molecular ions. Although the combination with a triple quadrupole mass spectrometer is briefly mentioned as a possibility, main attention is directed to a QqTOF, a combination of a mass filter (Q), a fragmentation cell (q), and time-of-flight mass analyzer (TOF) as the last mass analyzer, just as suggested by D. E. Clemmer.

A further ion mobility spectrometer has become known under the abbreviation "TIMS" (trapped ion mobility spectrometer). TIMS is a very small ion mobility spectrometer (the active part is only about five centimeters in length), quite different from both drift tubes at constant electric field and travelling wave mobility spectrometers. TIMS works with gas flow and electric counterfield and is thus more similar to the device of A. V. Loboda. In contrast to Loboda's device, an electric field profile with a ramped electric field barrier is used in a constant gas flow to hold back ions by their ion mobility; a decrease of the field barrier releases ions with increasing ion mobility, resulting in an ion mobility spectrum. The extraordinary and unique characteristic of ion mobility separators of the TIMS type is the fact that the ion mobility resolution continually increases with increasing scan duration. With TIMS, extraordinarily high ion mobility resolutions in the order of $R_{mob}=400$ have already been achieved experimentally. The TIMS is described in detail in U.S. Pat. No. 7,838,826 B1 (M. A. Park, 2008).

In co-pending U.S. patent application Ser. No. 14/931,163 ("Acquisition of Fragment Ion Mass Spectra of Ions Separated by their Mobility"; M. Mann et al., 2015), measuring methods for more than 300 fragment ion mass spectra per second with a TIMS-QqTOF are described with adjustable ion mobility resolution.

The instruments of the type QqTOF described so far all are high-priced instruments, a major share of the price being caused by the high-resolution mass analyzer. There is still a need for low-priced instruments and methods for the quantitative measurement of high numbers of characteristic fragment ions from proteolytic digests of proteins extracted from a biological sample, or from a complex food/fruit/vegetable matrix, to be tested for pesticides and other contaminants, without having to necessarily measure the whole fragment ion spectra.

Definitions

As usual in the mass spectrometric literature, the abbreviation "Q" stands for a quadrupole used as a mass filter and operated with radio frequency (RF) plus direct current (DC) voltages; whereas the abbreviation "q" concerns an RF quadrupole rod device essentially without DC voltages (sometimes called RF-only), used as ion guide or fragmentation cell. So the abbreviation "QqQ" stands for a triple quadrupole device with a fragmentation quadrupole between two mass filters, and "QqTOF" stands for a fragmentation quadrupole between a mass filter and a time-of-flight mass analyzer. Alternatively, the triple quadrupole instrument may be abbreviated $Q_1Q_2Q_3$, particularly when the three RF quadrupole devices should be numbered, as is common practice in the art.

In some cases, the simplified expression "ion mass" stands here for the more exact "charge-related ion mass" (the ion mass m divided by the number z of surplus elementary charges of the ion), or the usual "mass-to-charge ratio m/z".

The expressions "separator" and "separation" are used here for devices and methods which separate different substances or different ion species in time. Chromatography, capillary electrophoresis, and ion mobility spectrometry would fall under the definition of a separation method. The term "filter" is applied to devices and methods which are generally configured to let pass only selected ion species from a larger variety offered. An example is the RF quadrupole mass filter, capable of filtering ions by mass (though a skilled practitioner will understand that an RF quadrupole mass filter can usually also be switched into the RF-only mode having a comparatively broad bandpass characteristic).

The "mobility scan time" or "mobility scan duration" is defined as duration of an ion mobility scan over an interesting range of ion mobilities, usually the full range of the mobilities of the ions stored prior to the scanning.

The "ion mobility" K is defined as $K=v_d/E$, $v_d$ being the drift velocity in a drift tube, E the electric field strength in the tube. A "reduced ion mobility" $K_0$ is defined as ion mobility K at standard NTP conditions. The "ion mobility resolution" is defined as $R_{mob}=K/\Delta K$, $\Delta K$ being the width of the ion mobility signal at half height.

SUMMARY OF THE INVENTION

The invention provides new instrumentation and new measurement methods on the basis of triple-quadrupole mass spectrometers (abbreviated "QqQ" or "$Q_1Q_2Q_3$"). The invention proposes to couple the usual triple-quadrupole mass spectrometer to a trapped ion mobility separator ("TIMS") at a location upstream of the first quadrupole mass filter $Q_1$.

This ion mobility separator separates the ion species of a collected volume of ions temporally by their mobilities, forming a partly overlapping sequence of short pulses of ion species, thereby concentrating the ions of an ion species by a factor of about twenty to fifty, and separating them in time from most of the other ion species, thus considerably improving the signal-to-noise ratio.

Ions of a first selected ion species from the ion mobility scan may be picked in the correct time interval and the correct mass range (both calculated and predetermined) by the first RF quadrupole mass filter $Q_1$, fragmented in the RF quadrupole fragmentation cell (the second quadrupole $Q_2$), and a characteristic fragment ion species may be selected by the RF quadrupole mass filter $Q_3$, and measured at an ion detector, resulting in a quantitative statement for this ion species. Then a second ion species from the same ion mobility scan cycle may be picked in time and mass by $Q_1$, fragmented by $Q_2$, and quantitatively measured by a prominent fragment ion using $Q_3$, and so on with a third, fourth, fifth ion species, thus easily measuring the fivefold to twentyfold number of ion species compared to a triple-quadrupole mass spectrometer without ion mobility separator, and detecting each ion species with considerably increased signal-to-noise ratio and correspondingly increased sensitivity.

This measurement cycle may be repeated with a second, a third, a fourth volume of collected ions, and so on. If the triple quadrupole mass spectrometer is further coupled to a chromatograph, all interesting substances may be measured as usual at their calculated and predetermined right retention times, sampling the full substance peak for each substance. In a surprising variant of this measurement method, the run time of the chromatograph may be drastically shortened because the ion mobility separator aids in the separation of substances (albeit exploiting a different separation principle). If the run time is shortened by a factor of, say, about ten, the number of ion species in a chromatographic peak increases by about the same factor, but the substance ions are separated again by the ion mobility separator. A single triple quadrupole mass spectrometer with TIMS may offer a tenfold higher workload.

In certain types of sample mixtures, the ion mobility separator may even render any upstream substance separator, e.g. LC or GC, completely dispensable. A skilled practitioner will appreciate that such possibility may be economically extraordinarily interesting, such as for certain single reaction monitoring (SRM) applications.

A preferred embodiment uses a trapped ion mobility spectrometer with parallel ion accumulation as described in co-pending U.S. patent application Ser. No. 14/614,456 ("Trapping Ion Mobility Spectrometer with Parallel Accumulation", M. A. Park and M. Schubert), which is to be incorporated herein by reference in its entirety. TIMS with parallel accumulation (in the following abbreviated "PATIMS") does in fact collect and separate by ion mobility all ions of the ion source without any losses of ions. PATIMS further provides the unique possibility to prolong the ion accumulation duration to find more detectable ion species without decreasing the measuring capacity for characteristic fragment ions, thereby even increasing the ion mobility resolution. The ions are collected in an accumulator unit, almost identical to the scanning unit, at a ramp of an electric field barrier such that they get spatially separated by their ion mobility along the ramp. Therefore, the accumulated ions are less influenced by space charge than in accumulators used in the drift tube or traveling wave ion mobility separators. Of greatest importance, however, is the unique feature of TIMS that the longer accumulation period permits to increase the mobility resolution by choosing correspondingly longer mobility scan durations, e.g. 100 milliseconds scan duration with an ion mobility resolution of $R_{mob}=90$ instead of 20 milliseconds scan duration with $R_{mob}=60$. As a consequence of the higher number of ions collected and the better ion mobility resolution, more ion species can be detected and measured. Once an ion mobility scan is over (optionally after twenty to one hundred milliseconds or even more), the accumulated ions are transferred (in about a millisecond) from the accumulation unit to the ion mobility scanning unit, and the next ion mobility scan can be started. In total, a skilled practitioner will appreciate that it will be possible to achieve a measurement rate of more than 300 characteristic fragment ions per second.

In such an instrument, a number of ion species can be measured with a precision of quantification which is about fivefold to fiftyfold higher than that which can be measured by MRM (multiple reaction monitoring) with a triple quadrupole mass spectrometer without any ion mobility separation, in particular if large numbers of substances are to be quantified. A skilled practitioner will further recognize that a better signal-to-noise-ratio will be achievable, resulting in better sensitivity.

Such instrument is particularly suited for the well-known method for the measurement of substances in mixed samples of different probands carrying sample-specific mass tags on cleavable linkers which split off sample-specific reporter ions in the fragmentation cell. The relations of the abundances of the reporter ions reflect the relations of the concentration of the corresponding substance in the different samples. Coupled to a chromatograph, the instrument may measure many hundreds or even thousands of abundance ratios in a single chromatography run.

The complex substance mixture (sample) may be a proteolytic digest of proteins extracted from a biological sample, or may be a biological sample containing drugs and their metabolites, or a complex food/fruit/vegetable matrix, to be tested for pesticides and other contaminants. The samples with digest peptides, with drugs and metabolites, or with pesticides are usually separated by an upstream liquid chromatograph or electrophoresis unit. The prominent and characteristic fragment ions of selected precursor ions are used to quantify the corresponding substances by measuring the fragment ions along their chromatographic peaks.

The complex mixture may also be a mixture of evaporable substances separated in a gas chromatograph and ionized by chemical ionization (CI), e.g. toxic substances like polychlorinated biphenyls (PCBs) or the like.

Setting up such a targeted measurement method is facilitated by the fact that precursor masses are known a priori and determining retention times, fragment ion masses and optimal collision energies by calculation is similar to the common triple quadrupole method development. This is especially advantageous for the technical teaching disclosed herein because the TIMS scanning can be turned off and the actual physical device could be used as regular ion funnel for the purpose of method development. The additional step needed is to find the correct elution times of the precursor ions from the ion mobility separator. This can be achieved, for example, by setting up a SIM (single ion monitoring) on the triple quadrupole mass spectrometer during each TIMS cycle, and detecting the time of ion elution, and repeating this for each precursor ion of interest, Alternatively, the parameters for the measurement (e.g. retention times, ion mobility scan times, masses of the ion species) are first determined with a more expensive high-performance instrument comprising an identical chromatograph, an identical ion source, an identical accumulative TIMS, similar $Q_1Q_2$ quadrupoles, and a time-of-flight mass analyzer with orthogonal ion injection.

In a further embodiment, PATIMS is operated additionally with a zoom, either a temporal zoom as described in U.S. Pat. No. 8,766,176 B2 (D. A. Kaplan, M. A. Park, M. Ridgeway) or a spatial zoom as described in co-pending U.S. patent application Ser. No. 14/931,125 (O. Raether and M. A. Park), both of which are incorporated herein by reference in their entirety. In the spatial zoom mode, ions are accumulated in a special accumulator unit at a ramp of an electric field barrier. However, the ramp of the electric field barrier used for the spatial zoom is made flatter. A field peak at the end of the ramp keeps back ion species of low mobility during ion accumulation. Ion species of a selected mobility range are accumulated on a part of the ramp having a much smaller field gradient compared to the field peak. The ion species of the selected range of ion mobilities are spatially decompressed to reduce the effects of space charge, allowing for the undisturbed collection of much more ion species in the selected ion mobility range using longer accumulation duration. The spatial zoom allows for the undisturbed detection and collection of still higher numbers of ions in selected ion mobility ranges during longer accumulation periods. At the same time, the ion mobility resolution furthermore increases, because a smaller range of mobilities is scanned with lower speed. The method makes ions detectable which cannot be seen in any operation mode of any other commercial mass spectrometer with ion mobility separator. The selected ion mobility ranges of the spatial zoom can be adapted to the ion mobility distribution of the ion species generated from the substance mixture.

The mass filters $Q_1$ and $Q_3$ are preferably fast-switching RF quadrupole rod mass filters. RF quadrupole rod mass filters may be switched, preferably in far less than a millisecond, to the mass of the ion species to be measured next in such a way that the transmission through the mass filter first is closed, then tuned to the next mass, and then opened again at the beginning of the calculated and predetermined correct time interval of the next ion species to be measured. In this way, the mass filter can pick up an ion species in the correct time interval and the correct mass range, both of which have been calculated and predetermined.

The fragmentation cell $Q_2$ is preferably a flow-through cell in which the ions are not trapped. The ions are preferably fragmented by collision induced dissociation in a cell filled with an inert collision gas, but can also be fragmented by electron impact or photon induced dissociation (either by using infrared or ultraviolet light sources). In some triple quadrupole instruments, the fragmenting quadrupole forms a semicircle, such as bent by 180 degrees, allowing for the arrangement of the two mass filters in parallel to form a small instrument having a small footprint on the laboratory desk.

DETAILED DESCRIPTION

Figure 1:
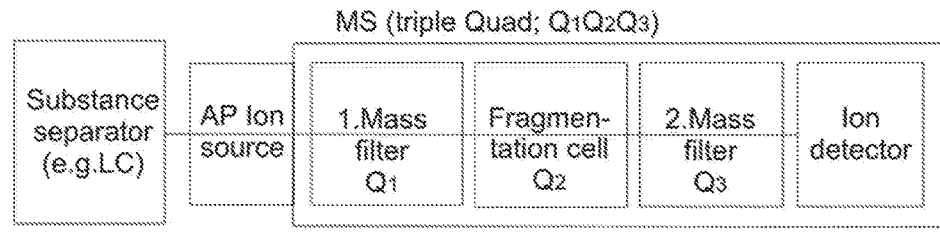
FIG. 1 shows a schematic overview of a usual triple quadrupole mass spectrometer according to the state of the art, with an upstream substance separator, e.g., an LC, an atmospheric pressure (AP) ion source, the three quadrupoles $Q_1$, $Q_2$, and $Q_3$, and an ion detector.
Figure 4:
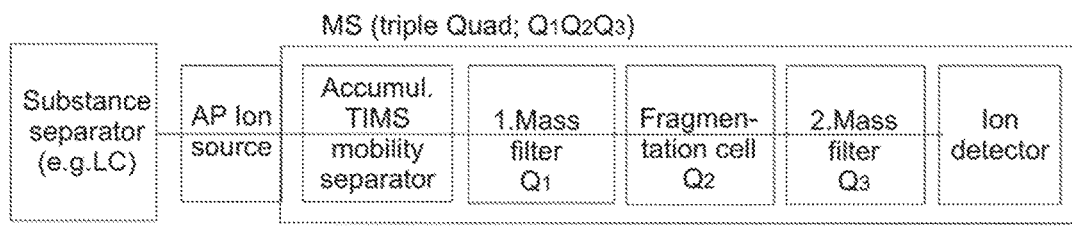
FIG. 4 shows a schematic overview of the new triple quadrupole mass spectrometer according to principles of this invention, in a preferred version having an accumulative TIMS ion mobility separator (PATIMS) in front of the three quadrupoles.

The invention provides new instrumentation and new measurement methods on the basis of triple-quadrupole mass spectrometers (here abbreviated "$Q_1 Q_2 Q_3$"), exposing a number of unexpected advantages. A usual triple-quadrupole mass spectrometer, as presented in FIG. 1, is coupled upstream of the first quadrupole mass filter $Q_1$, as shown in FIG. 4, to a spatially short ion mobility separator, preferably a trapped ion mobility spectrometer ("TIMS") as described in detail in U.S. Pat. No. 7,838,826 B1 (M. A. Park, 2008).

Figure 2:
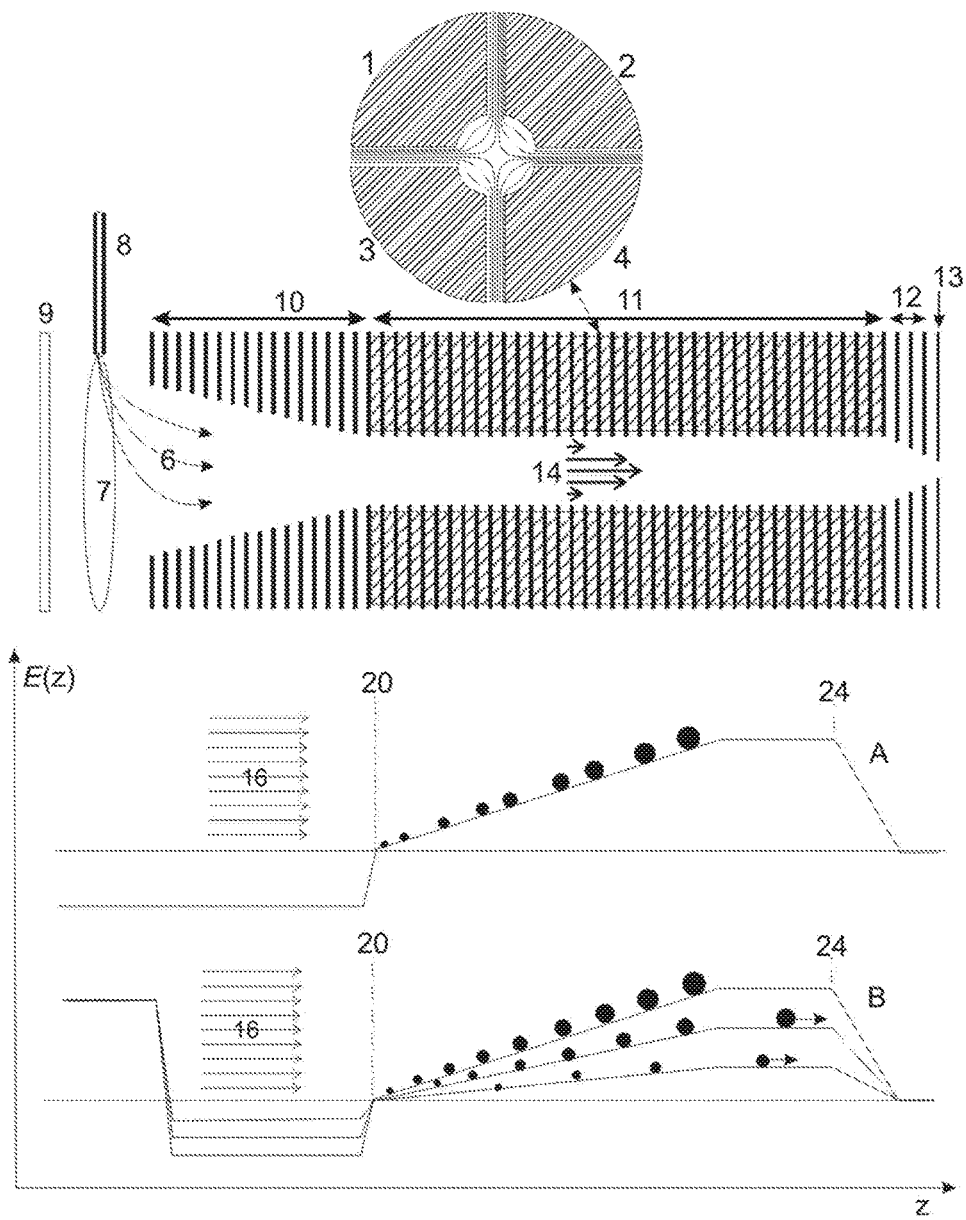
FIG. 2 schematically illustrates design and operation of a trapped ion mobility spectrometer (TIMS) according to the state of the art, as described in U.S. Pat. No. 7,838,826 B1 (M. A. Park, 2008). The ion mobility scanning tube (11) between entrance funnel (10) and exit funnel (12) amounts to only 48 millimeters in length; the inner diameter amounts to eight millimeters. The ion mobility scanning tube (11) consists of a series of segmented diaphragms with quadrant electrodes (1) to (4) as shown at the top of the figure, to generate a quadrupolar RF field inside the tube. Ions (6) from an ion source (not shown) are introduced through capillary (8) together with a gas stream (7) into a first vacuum chamber. A repeller plate (9) directs the ions (6) into the funnel (10); the gas flow (14) inside the tube, having a parabolic flow speed distribution, drives the ions into and through the ion mobility scanning tube (11). In the two diagrams E(z)=f(z) in the bottom part of the figure, z here being the coordinate along the axis of the device (and not the charge number), the electric field profiles are shown for two phases of operation: In the accumulation phase (A) ions are blown by the gas flow (14, 16) onto the rising edge ("ramp") of the electric field profile between z locations (20) and (24). In the scan phase (B), a steadily or step-wise gradually decreasing electric field profile voltage releases ions in the order of increasing mobilities over the field plateau at location (24) and through the exit funnel towards an ion detector (not shown). Ion current measurements vs. time result in ion mobility spectra from low mobilities to high mobilities.

The principle and operation of the trapped ion mobility spectrometer TIMS are outlined in some detail in FIG. 2. The ion mobility separator first collects ions (6) blown entrained in a blowing gas (14, 16) against an electric DC field ramp between positions (20) and (24) inside the TIMS accumulation and scanning unit (11), as shown in the electric DC field profile indicated as Diagram A. The ions gather each at a location with equilibrium of electrical force and friction force of the blowing gas. Ions with lowest mobility, usually the largest ions, collect at the end of the ramp, as indicated by the size of the dots on the ramp. The ions are accumulated separated by their ion mobilities thus reducing ion density and space charge effects. In a subsequent phase, viz. the scanning phase, the electric field profile is continuously decreased from highest voltage to zero in about 20 milliseconds (or longer), releasing the collected ion species one after the other according to their mobilities, as indicated in Diagram B. The ion species thus are temporally separated by their ion mobilities, forming short pulses of about one millisecond in length for each of the ion species, thereby concentrating all ions of an ion species in a short time interval by at least a factor of twenty, and separating them in time from most of the other ion species, thus considerably improving the signal-to-noise ratio. To utilize all ions from an ion source, an accumulation device such as an ion trap may be used upstream of the TIMS device to accumulate ions during the scan of TIMS.

Figure 3:
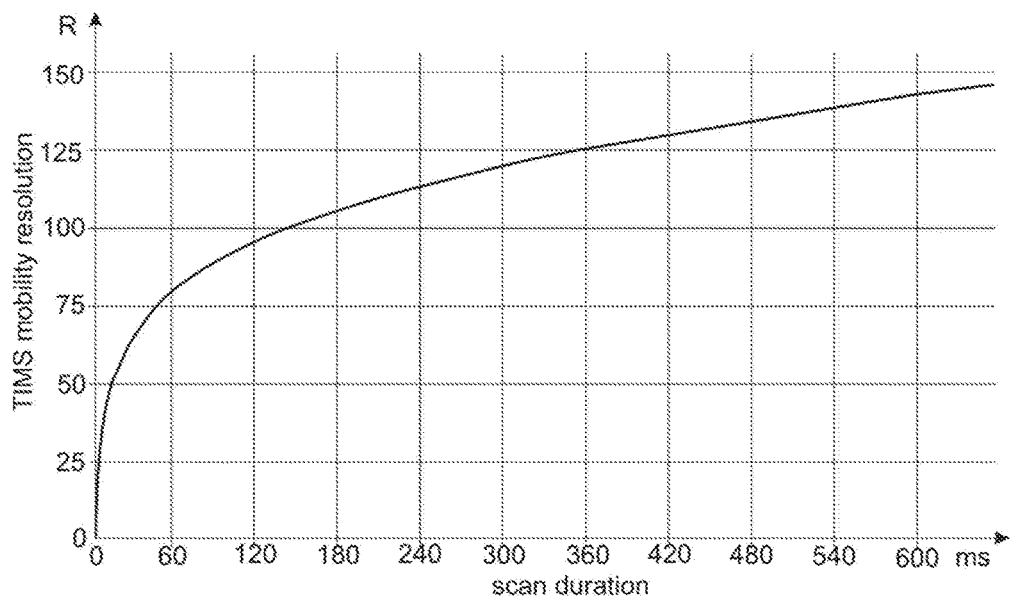
In FIG. 3, the ion mobility resolution of the TIMS instrument is plotted as function of the duration needed for a scan over the full range of ion mobilities. With a scan duration of only 20 milliseconds, a mobility resolution of about $R_{mob}=60$ is achieved for an ion species with an ion mobility of $K_o=0.5$ m$^2$/Vs, with 300 milliseconds scan duration, the resolution rises to $R_{mob}=120$.

A unique feature of TIMS is that a longer scan period permits an increase in the mobility resolution, e.g., 100 milliseconds scan duration with an ion mobility resolution of $R_{mob}=90$ instead of $R_{mob}=60$ with 20 milliseconds scan duration. The diagram in FIG. 3 presents the ion mobility resolution $R_{mob}$ as a function of the time needed to scan the full range of ion mobilities. As a consequence of the better ion mobility resolution, more ion species can be detected above the limit of detection, and measured. The ion accumulation device upstream of the TIMS device should be able to collect the ions even during the longer scan periods without showing losses of ions due to space charge effects.

The resulting instrument according to the invention is presented schematically in FIG. 4. The trapped ion mobility separator TIMS, in this case a TIMS with parallel accumulation ("PATIMS"), is inserted between the ion source and the triple quadrupole assembly, here directly in front of the first quadrupole $Q_1$. With this instrument, a number of ion species can be measured quantitatively which is, comparing measurements with the same precision, at least tenfold higher than that which can be measured with a triple quadrupole mass spectrometer not being coupled to any ion mobility separator. A skilled practitioner will recognize that a considerably better signal-to-noise-ratio can be achieved, resulting in better sensitivity.

Figure 5:
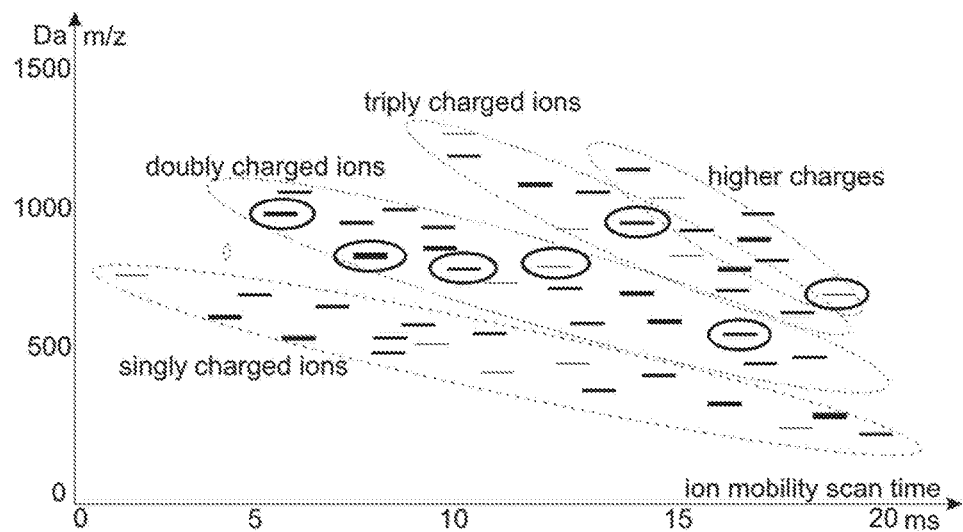
FIG. 5 presents schematically a mass-mobility map of a complex mixture of ion species, separated by a TIMS ion mobility spectrometer, showing the whole range of ion mobilities from low mobilities to high ion mobilities. Ion species with single charges appear to be separated from ion species with higher charges. As a rule, multiply charged ions of ion species with the same m/z appear to have higher ion mobilities. Such maps can be measured stepwise using the TIMS mobility separator and one of the quadrupole filters, stepping through the mass range of interest in subsequent measurement cycles, without fragmenting the ions. An easier method to obtain this mass-mobility map uses a mass spectrometer system comprising an identical chromatograph, an identical ion source, an identical TIMS, a similar mass filter $Q_1$, a similar fragmentation cell $Q_2$, and a time-of-flight mass analyzer which can acquire the full fragment ion spectrum for each time interval. A scan duration of 20 milliseconds achieves an ion mobility resolution of about $R_{mob}$=60. An ion species pulse length of about 1.0 milliseconds and a switching time for $Q_1$ of 0.7 milliseconds allows up to eleven ion species to be selected for the measurement of characteristic fragment ions.

The separation capability of a TIMS ion mobility separator can be seen in FIG. 5, presenting a so-called "mass-mobility map" of a complex mixture of ion species separated in 20 milliseconds only by the TIMS ion mobility spectrometer. FIG. 5 shows the masses of the ion species over the whole range of ion mobilities (about $0.5 < K_0 < 1.0$ $m^2/Vs$) with an ion mobility resolution of about $R_{mob}=60$.

In the practice of TIMS-triple-quadrupole operation, when merely a targeted analysis is performed, the determination of a complete mass-mobility-map as shown in FIG. 5 may however be dispensable. In such case, only compounds the masses of which are known beforehand have to be measured. Then, the triple quadrupole mass spectrometer does not need to determine the precursor ion masses, it only needs to determine the time when each of precursor mass elutes from the TIMS cell.

As can be seen from FIG. 5, the mass-mobility map for 20 milliseconds scan duration allows up to eleven ion species to be selected for the measurement of characteristic fragment ions, if the opening interval for the first mass filter $Q_1$ is chosen to be one millisecond, and the switching time of the mass filter $Q_1$ to the next selected ion species amounts to 0.7 milliseconds.

In a fresh measuring cycle with the instrument of FIG. 4, the ions are separated by the TIMS device, and the ions of a first ion species, selected from the mass-mobility map in FIG. 5, may be picked in the correct time interval and the correct mass range (both calculated and predetermined) by the quadrupole mass filter $Q_1$. The mass range may embrace all isotopic variants of the ion species. The ions of this species may be fragmented in the quadrupole fragmentation cell (the second quadrupole $Q_2$), and a prominent and characteristic fragment ion species may be selected by the mass filter $Q_3$, and measured at an ion detector. Then a second ion species from the same ion mobility scan may be picked in its time interval and its mass range, fragmented, and quantitatively measured by a prominent fragment ion, and so on with a third, fourth, fifth ion species, thus easily measuring a number of ion species higher by up to tenfold than with a triple-quadrupole mass spectrometer using SIM (single ion monitoring) not being coupled to any ion mobility separator. If a triple quadrupole mass spectrometer without mobility separator uses MRM (multiple reaction monitoring), the precision of the measurements inevitably decreases with the number of reactions measured because the number of ions measured likewise decreases. This is not the case using a triple quadrupole assembly coupled to TIMS.

The number of ions collected by any upstream ion collection unit such as an ion trap and the transfer to the ion mobility separator is greatly limited by the effect of repelling Coulomb forces between the accumulated ions, in short called "space charge effect". To overcome problems with space charge, preferred embodiments of the invention use the TIMS device with parallel accumulation ("PATIMS") as described in co-pending U.S. patent application Ser. No. 14/614,456 ("Trapping Ion Mobility Spectrometer with Parallel Accumulation", M. A. Park and M. Schubert). PATIMS allows for the collection of more ions than usual ion accumulators because the ions are already accumulated separated by their ion mobility and consequently less influenced by space charge. As long as the accumulation periods are not excessively long, this device uses almost all ions delivered by the ion source for measurements, i.e., these modes show highest sensitivity and highest ion utility rates.

Figure 6:
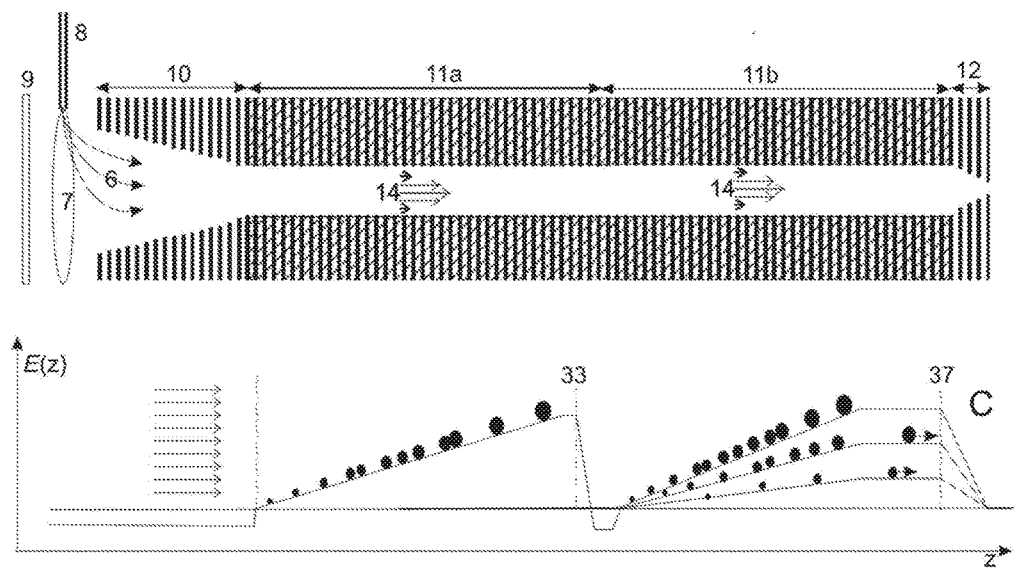
FIG. 6 schematically depicts an embodiment of the mobility spectrometer presented in co-pending U.S. patent application Ser. No. 14/614,456 ("Trapping Ion Mobility Spectrometer with Parallel Accumulation", M. A. Park and M. Schubert). Ions are introduced through entrance capillary (8) entrained by gas (7) into the first vacuum stage of the mass spectrometer. The entrained ions (6) are pushed by repeller (9) through an RF ion funnel (10) into the trapping ion mobility spectrometer (11). The trapping ion mobility spectrometer comprises an elongated tunnel (11), divided into an ion accumulation unit (11a) and an ion mobility scanning unit (11b). A gas flow (14) drives the ions through the elongated tunnel (11). The spectrometer furthermore comprises an RF voltage supply unit (not shown) for RF voltages at quadrants of the tunnel electrodes and DC voltage supply units (likewise not shown) for the generation of the electric field barrier in axial direction within the two tunnel units, contacting the electrodes at locations (33) and (37). A quadrupolar RF field inside the tunnel (11) holds the ions near to the axis of the device. Chains of resistors between the diaphragms in both tunnel units produce the two electric DC field barriers for the ion accumulation unit (11a) and for the ion mobility scanning unit (11b), shown in diagram (C) at the bottom of the figure. The gas flow (14) drives the ions against the ramps of the electric field barriers, separating the ions by their ion mobility. During the ion mobility scan, the voltage applied to electrode (37) of the scan unit (11b) is steadily or step-wise gradually decreased, thereby releasing ion species with increasing mobility, resulting in an ion mobility spectrum. During the ion mobility scan, the accumulation unit accumulates fresh ions which can be transferred within about a millisecond by the gas flow to the scanning unit at the end of the scan.

An exemplary embodiment, therefore, uses a trapped ion mobility spectrometer with parallel ion accumulation (PATIMS), an embodiment being presented schematically in FIG. 6. A volume of ions is collected in the accumulator unit (11a) at the ramp of a first electric field barrier (up to location (33)) such that the ion species get spatially separated by their ion mobility along the ramp. The first ramp is created by a DC voltage fed to location (33); the ramp is formed by a voltage divider consisting of a series of resistors. The accumulated ions are less influenced by space charge than in other types of ion accumulators. During the ion accumulation, another volume of ions, accumulated before, is scanned in the scanning unit (11b), delivering the short ion pulses with ion species separated by their ion mobility. At the end of the scanning time, the voltage at location (37) is restored, the voltage at location (33) is switched off, and the ions accumulated in the accumulating unit (11a) are transferred, within about one millisecond, by the blowing gas to the scanning unit (11b). This parallel accumulation PATIMS utilizes all ions generated by the ion source with only negligible losses: Once an ion mobility scan is over (optionally after about twenty to one hundred milliseconds), the accumulated ions are transferred (in about a millisecond) from the accumulation unit (11a) to the ion mobility scanning unit (11b), and the next ion mobility scan can be started. The total length of accumulation unit (11a) plus scanning unit (11b) can amount to about ten centimeters only.

With such instruments as illustrated in FIG. 4, the time needed to measure a characteristic fragment ion, with switching the quadrupole filter $Q_1$ to the new mass range, letting pass the selected ion species, fragmenting the ions of this selected ion species in quadrupole $Q_2$, and measuring the characteristic fragment ions by mass filter $Q_3$, may amount to about 1.7 milliseconds only. Furthermore, a time of about 1.5 milliseconds is needed for the transfer of ions from the accumulator unit (11a) to the ion mobility scanning unit (11b), and to dampen the ion movements within the gas flow at their new location. A measurement procedure operating with 20 milliseconds ion mobility scan duration and 1.5 milliseconds transfer time, i.e., with 21.5 milliseconds per cycle, results in about 46 measurement cycles per second with a maximum measurement capacity of eleven fragment ion mass spectra each. Thus the measurement capacity amounts to 46×11=506 characteristic fragment ions per second, outperforming any mass spectrometer with state-of-the-art mobility separator known to the Applicant.

This capacity of 506 characteristic fragment ions per second for the basic operation mode with 20 milliseconds scan duration is an approximation only, strongly dependent on the time needed for a single measurement of a fragment ion mass spectrum. If this time, assumed to be 1.7 milliseconds, must be elongated to 2.0 milliseconds for whatever reason, the capacity decreases to about 460 fragment ion measurements per second. The true capacity may amount to a number between about 350 and 500 characteristic fragment ions per second. In experiments with a similar instrument, comprising a time-of-flight mass spectrometer instead of $Q_3$, a capacity of 380 full fragment ion mass spectra per second was found. In practice, this measurement capacity will rarely be fully utilized.

PATIMS with parallel ion accumulation provides the unique possibility to use longer accumulation durations with the advantage that the correspondingly slower ion mobility scan increases the ion mobility resolution. With longer accumulation and ion mobility scan durations, the number of accumulated ions increases and the mobility resolution is improved, resulting in a better detectability because the signal-to-noise is increased by a higher compression of the ions in the short pulses of the ion mobility peaks, in spite of the fact that the pulse length of ions of one species increases slightly. Therefore, the sensitivity increases and more ion species can be detected in the corresponding mass-mobility map. If the accumulation duration is increased to 100 milliseconds, and a single measurement is assumed to take about 2.0 milliseconds (instead of the 1.7 milliseconds for short scans), about ten measurement cycles with about 50 fragment ion mass spectra each can be performed in a single second with five times more ions in the mass-mobility map. Interestingly, if the fragment ion mass spectrum acquisition time is slightly increased to exactly 2.0 milliseconds, the measurement capacity results in about 10×50=500 characteristic fragment ions per second, i.e., the measurement capacity keeps about constant when accumulation and scan durations are increased. Five times more ions per cycle increases the number of detectable ion species in the mass-mobility map considerably; the exact improvement depends on the mixture of substances. It is, however, justifiable to assume that the number of detectable ion species increases by at least a number of two.

Figure 7:
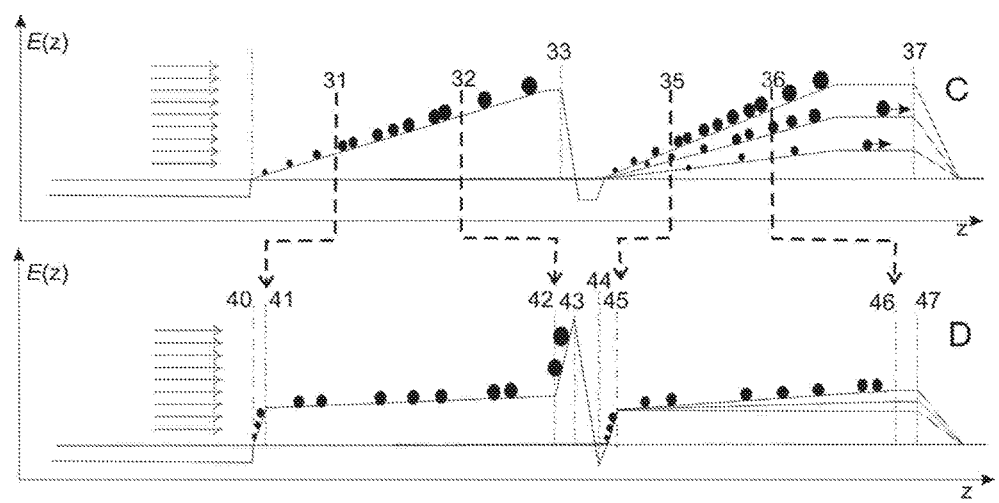
FIG. 7 illustrates the operation of a spatial zoom mode preferably used for this invention, presenting an electric field barrier (C) for the usual operation without spatial zoom, and a barrier (D) for the zoomed operation. The spatial zoom is based upon field barrier (D) exhibiting a wide and flat electric field gradient (a flat ramp) positioned between z-locations (41) and (42) and a field peak with steep field gradient between (42) and (43), keeping back ions of low mobility during ion accumulation. Ions of an interesting range of ion mobilities between locations (31) and (32) of the non-zoomed barrier (C) are accumulated on the flat ramp of the field barrier between (41) and (42). The ions are spatially decompressed to reduce the effects of space charge, allowing for the undisturbed collection of much more ions using longer accumulation durations. The ion mobility scanning unit (11b) shows a similar electric field profile, however without the field peak. Once the ions stored between (45) and (46) are scanned according to their ion mobility, the ions of the accumulation unit are transferred, in about a millisecond, to the ion mobility scanning unit (11b), thereby letting pass the non-interesting ions of low mobility stored at the ramp of the peak between locations (42) and (43). The ion species stored between locations (45) and (46) can be scanned much slower than usual, resulting in a high ion mobility resolution.

Although the accumulation of ions on the electric field ramp decompresses the ion species and reduces the effect of space charge, there remain limits for the number of accumulated ions. If the accumulation of ions is impaired by space charge, a "spatial zoom mode" further offers an improved mode of operation. In case of overcrowding the accumulator with ions, the spatial zoom mode is the preferred mode of operation. The spatial zoom is a particularly favorable mode of operation based upon field barriers shown in Diagram D of FIG. 7 exhibiting a wide and flat electric field gradient positioned between z-locations (41) and (42) and a field peak with steep field gradient between (42) and (43), keeping back ions of low mobility during ion accumulation. Ions of an interesting range of ion mobilities, for instance between locations (31) and (32) of the non-zoomed profile in Diagram C of FIG. 7, are accumulated on the flat part of the field barrier between (41) and (42). The ions are spatially decompressed to reduce the effects of space charge, allowing for the collection of many more ions using longer accumulation times. The adjacent ion mobility scanning unit (11b) shows a similar electric field barrier, however, without the field peak. Once the ions stored between (45) and (46) are scanned according to their ion mobility, the ions of the accumulation unit are transferred, in about a millisecond by switching off the voltage at locations (41-43), to the ion mobility scanning unit, thereby letting pass the non-interesting ions of low mobility stored at the ramp of the field peak. The ions collected between locations (45) and (46) then can be scanned with very low scanning speed and correspondingly high ion mobility resolution.

Figure 8:
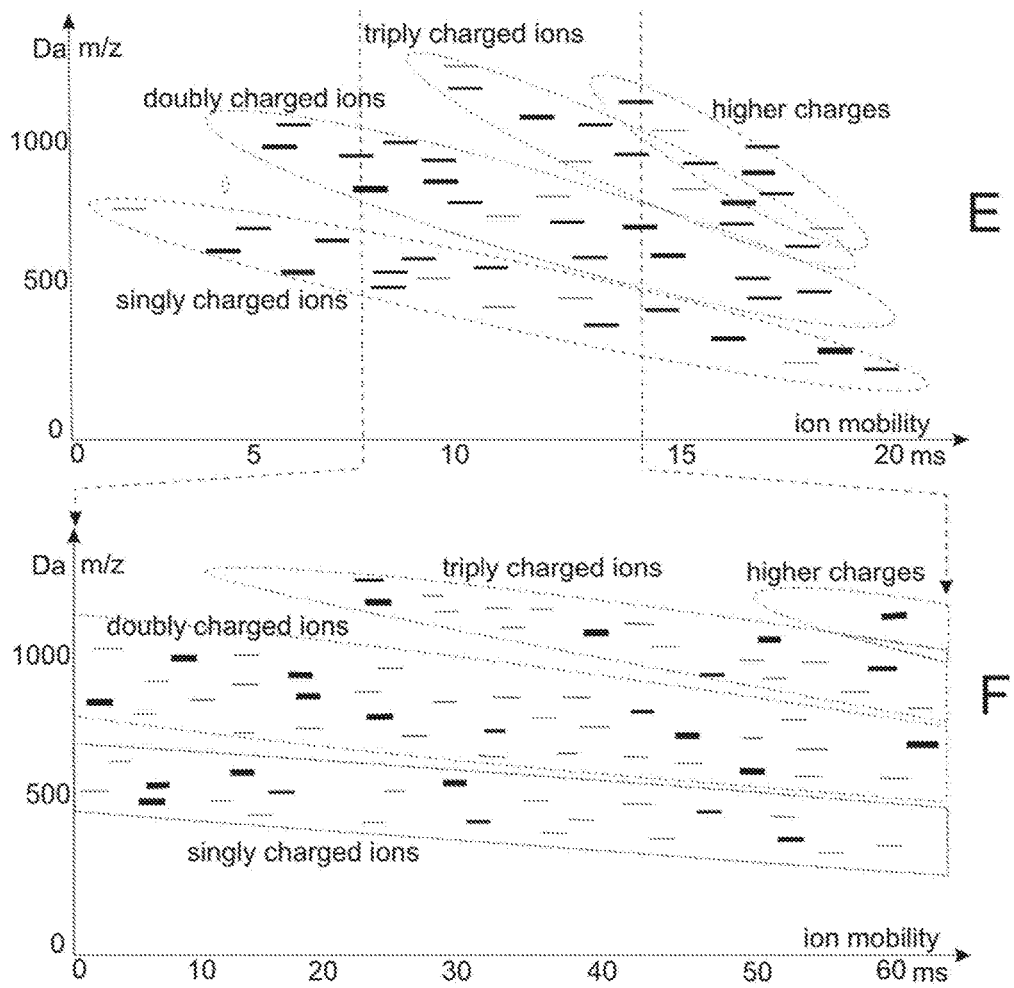
FIG. 8 schematically presents in the upper part (E) a mass-mobility map showing the whole range of mobilities, and in the lower part (F) a mass-mobility map with higher ion mobility resolution restricted to about ⅓ of the full range of ion mobilities and with three times longer accumulation and scan duration by application of a spatial zoom. Such maps can be measured stepwise as described above, or by using an identical TIMS mobility separator coupled to a time-of-flight analyzer. The ion mobility range of the mass-mobility map (F) in the lower part represents only ⅓ of the full mobility range by applying correctly selected voltages to the ends of the flat ion accumulation or ion mobility scanning regions. By a three times longer accumulation period of 60 milliseconds three times more ions are collected, and by a nine times slower scan speed (corresponding to 180 milliseconds for the total mobility range), a mobility resolution $R_{mob} \geq 100$ is achieved, both increasing detectability. Considerably more ion species can be detected and selected in the corresponding mass-mobility map; the exact improvement depends on the mixture of substances. Within a single measurement cycle of 60 milliseconds, at least 24 ion species may be selected for the measurement of a significant fragment ion in each measurement cycle.

As an example for the application of the spatial zoom mode, the ion mobility range of the mass-mobility map F in the lower part of FIG. 8 represents only ⅓ of the full mobility range of mass-mobility map E by applying correctly selected voltages to the ends of the flat ion accumulation or ion mobility scanning regions. By a three times longer accumulation period of 60 milliseconds about three times more ions are collected, and by a nine times slower scan speed (corresponding to a full scan duration of 180 milliseconds for the total mobility range), a mobility resolution $R_{mob} \geq 100$ is achieved. Considerably more ion species can be selected for a single measuring cycle. Thus more ion species can be detected, selected and measured in a single measurement cycle by this procedure. The measurement capacity still amounts to about 350 to 500 characteristic fragment ions per second, but by the strongly increased detectability, many more characteristic fragment ions can be measured; fragment ions of precursor ions which cannot be detected in state-of-the-art measuring devices and modes, not even in the other operation modes of TIMS. The range of ion mobilities of the spatial zoom mode may be altered during a run of the substance separator.

The complex substance mixture is typically a proteolytic digest of proteins extracted from a biological sample, or a biological sample tested for drugs and their metabolites, or a complex food/fruit/vegetable matrix tested for pesticides and other contaminants. The substance separation of these mixtures is usually performed by a liquid chromatograph (HPLC). Other mixtures concern samples with evaporable substances, e.g., polycyclic biphenyls, using a gas chromatograph (GC) as substance separator. The characteristic fragment ions of the analyte ions are used to quantify the corresponding substances by measuring the fragment ions along the chromatographic peak.

Triple quadrupole instruments are mostly used to measure substances which are exactly known beforehand. Such a measurement is usually called a "targeted measurement". Setting up such a targeted measurement with the instrument of FIG. 4 according to this invention requires the knowledge of at least a part of the mass-mobility map (FIG. 5) with identification of the targeted ion species. For a targeted substance, several parameters have to be known (that is, calculated and predetermined): the time interval of appearance of the substance ions during the ion mobility scan, the mass of the substance ions, the mass of the characteristic fragment ions, the optimal collision energy and finally the chromatographic retention time if a chromatograph is used upstream of the TIMS cell.

The common way to set up a targeted analysis (structure and precursor ion masses are known) in a triple quadrupole mass spectrometer without TIMS involves the following steps: 1—setting up a full scan of the ions eluting in substance peaks of chromatographic separation in the mass filter $Q_1$, 2—determining retention times and retention time windows for each target compound from the full scan chromatogram, 3—setting up survey fragment ion scans for each compound at the correct retention time and using the optimal precursor ions and a range of collision energies, 4—determining best fragment ions and optimal collision energies from the fragment ion scans, 5—finally setting up MRM (multiple reaction measurement) scans with optimal parameters: retention times and retention time windows, precursor and fragment ions, collision energies, and optimal collection (dwell) times. This exact procedure can be followed using the instrument of FIG. 4 by disabling the TIMS scanning scheme, in which case the TIMS device acts like a regular ion funnel. The additional step required by the addition of TIMS is to determine the scan elution time for each target ion released by the TIMS cell. This can be determined, for example, by performing a rapid TIMS scan (e.g., 20 ms) while holding the $Q_1$ of the triple quadrupole mass spectrometer at the first target mass and determining the ion arriving time, then repeating this procedure for each of the other targeted precursor masses in a retention time window. In this way, the MRM method is replaced by the ion mobility separator TIMS, resulting in the measurement of more ions, better signal-to-noise ratio, and better sensitivity.

If instrumentation is available, the parameters of the targeted substances needed for setting up the measurement may be determined with a different instrument. This instrument should comprise an identical substance separator (chromatograph or electrophoresis capillary), an identical ion source, an identical parallel accumulation PATIMS, similar $Q_1$ and $Q_2$ quadrupoles, and a time-of-flight mass analyzer with orthogonal ion injection. The time-of-flight analyzer is able to measure the complete fragment ion spectrum, thus permitting (1) identification of the precursor ion species and (2) selection of a suitable characteristic fragment ion. With this instrument, all necessary parameters can be determined: The retention times of the targeted substances in the substance separator, the ion mobility scan intervals obtained by TIMS, the mass range of the precursor ion species, and the mass range of a characteristic fragment ion. With a single high-price high-performance TIMS-$Q_1Q_2$TOF mass spectrometer all necessary measurement parameters for a whole series of low-price TIMS-$Q_1Q_2Q_3$ mass spectrometers can be obtained.

During the setup of a preferred operation method for the measurement of a multitude of target substances during the run of a substance separator, e.g., an LC, the duration of the TIMS scans may be varied as a function of the substance separator run time, because usually less targeted substances appear in the beginning, lots of compounds in the middle, and less targeted compounds toward the end of the LC run. The triple quadrupole mass spectrometer can vary the TIMS scanning times based on the density of chromatography peaks to optimize signal-to noise ratio. If only a few substances have to be measured in parallel, a short scan duration of 20 to 40 milliseconds may be chosen, with a high number of repetition cycles per second; for a higher number of target substances overlapping in the eluent of the substance separator, or for a method with highest sensitivity, a longer scan duration is to be preferred, with lower numbers of repetitions per second.

If the mixture is extremely crowded, a spatial zoom may be chosen. Because the mixture of substances changes continuously in composition during an LC run, the molecular weights vary, in the average, from low mass substances to substances of higher mass. Therefore, also the average ion mobility will vary along the LC run. This variation may be considered by the selection of the ion mobility ranges for the spatial zoom mode.

In a similar manner, a temporal zoom may be applied, scanning rapidly over ranges of ion mobilities without interest, and slowing down the scan speed in interesting ion mobility ranges. In total, the scan duration is shortened but the ion mobility resolution around the targeted precursor ions is increased.

The triple quadrupole mass spectrometer coupled to parallel accumulation TIMS (PATIMS) surprisingly offers a further essential economic advantage. The possibility to vary accumulation and scan durations, and the possibility to select interesting ion mobility ranges, permits one to drastically shorten the substance separator runs, i.e., HPLC or capillary electrophoresis runs. The number of overlapping substances in the separator peaks increases greatly, but the separation of substances by TIMS compensates by its additional substance separation. The application of temporal or spatial zoom helps to separate the targeted substances from others of lesser interest. For instance, an HPLC run of three hours may be shortened to about 18 minutes, increasing the work load by a factor of ten. The number of overlapping substances eluting as a single peak increases, but the ion mobility separator helps in separating the substances again. A run time of 18 minutes presented here is only an example, in practice short HPLC runs of a few minutes may be used, shortening the analysis time drastically.

In certain types of sample mixtures, for instance in food mixtures tested for pesticides, the ion mobility separator may even render any upstream substance separator, e.g., any LC or GC, completely dispensable. Such measurement procedures of significantly shorter duration offer high economic advantages.

Such an instrument may be particularly suited for the measurement of relative abundances of peptides in mixed samples of different probands comprising sample-specific mass tags on cleavable linkers which split off sample-specific reporter ions in the fragmentation cell (see, e.g., "Isotope-coded chemical reporter and acid-cleavable affinity reagents for monitoring protein sulfenic acids"; T. H. Truong et al., Bioorganic & Medicinal Chemistry Letters 21 (2011) 5015-5020). These (and other) quantification methods use labeling peptides of interest with isobaric mass tags via cleavable linkers. The linkers used for the different proband samples may split at different sites during fragmentation, producing reporter ions of slightly different masses. These reporter ions with different masses can be measured in mass filter $Q_3$. The relations of the abundances of the reporter ions reflect the relations of the concentration of the corresponding peptide in the different samples. Coupled to a chromatograph, the instrument may measure many hundreds or even thousands of abundance ratios in a single chromatography run.

The technical teaching presented herewith basically pertains to a mass spectrometer, comprising an ion source of the type being configured to continuously generate ions from a sample being supplied thereto, a trapped ion mobility separator (TIMS) being configured to receive the generated ions in accumulated volumes thereof and further being configured to output these accumulated volumes in short pulses of ion species that have been separated in time by their ion mobility, a first mass filter, such as a quadrupole mass filter $Q_1$, being configured to receive the ion species and select precursor ions therefrom to be fragmented, a fragmentation cell, such as a quadrupole fragmentation cell $Q_2$, being configured to receive and fragment the selected precursor ions, a second mass filter, such as a quadrupole mass filter $Q_3$, being configured to receive and select fragment ions resulting from the precursor ions by the fragmentation, and an ion detector being configured to receive and measure an ionic output from the second mass filter.

An exemplary embodiment comprises configuring the trapped ion mobility separator to use parallel ion accumulation (PATIMS), wherein ions are accumulated in an accumulation unit separated by their ion mobility while scanning the ions according to their ion mobility in a subsequent scanning unit, and the ions are transferred, after each scan, in about a millisecond from the accumulation unit to the scanning unit. The mass spectrometer may be coupled to a substance separator, wherein the substance separator may be a gas chromatograph, a liquid chromatograph, or a capillary electrophoresis device.

The mass spectrometer should comprise RF and DC voltage generators for the quadrupole mass filters capable to switch the mass filters within less than a millisecond from filtering a first ion species to filtering a second ion species. Preferably the switching time up to equilibrium should be in the order of 500 to 700 microseconds. Favorably, the RF and DC voltage generators deliver voltages for the switching process of the first mass filter from filtering one ion species to filtering another ion species, which first close the first mass filter, then adjust it for filtering the next ion species, and open it at the correct time interval of the next ion species. The opening and closing of the first mass filter may be performed by a slight increase and decrease of the DC voltage relative to the RF voltage.

In various embodiments, the (continuous) ion source is one of an electrospray ion source, chemical ionization source, photoionization source, and electron ionization source.

The invention further concerns a method to cyclically and quantitatively measure characteristic fragment ions of a multitude of selected precursor ions in a mass spectrometer according to the description given above during a single ion mobility scan of the trapped ion mobility separator (TIMS), comprising the steps: a) filling the trapped ion mobility separator (TIMS) with an accumulated volume of ions, b) scanning the accumulated volume of ions according to their ion mobilities, thereby generating pulses of ion species with different ion mobilities, c) switching the first mass filter to filter, in the correct time interval and correct mass range, the ions of a selected ion species appearing next during the scan, and switching the second mass filter to the correct mass range of the characteristic fragment ion of this ion species, d) fragmenting the filtered ions of the selected ion species in the fragmentation cell, filtering the characteristic fragment ions in the second mass filter, and measuring the resultant ionic output with the ion detector, and e) repeating steps c) and d) as long as there are still selected but unmeasured ion species.

Furthermore, the invention relates to a multi-cycle method cyclically performing the measurement cycle until a given time period is over, or a given maximum number of measurement cycles are performed, or a selected ion species can no longer be detected.

In a preferred embodiment, the multi-cycle method accumulates and scans ions in parallel in a trapped ion mobility separator with parallel ion accumulation (PATIMS), and transfers the accumulated ions, after the end of a scan, in about a millisecond from the accumulation unit to the scanning unit. The multi-cycle method may even operate in the spatial zoom mode, accumulating and scanning ions in a preselected range of mobilities only.

A special multi-cycle method measures the relative abundances of substances in samples, which were mixed from various probands and tagged sample-specifically by isobaric tags with linkers cleavable at sample-specific sites, by measuring the reporter ions, stripped in the fragmentation cell from the tagged substance ions.

The multi-cycle method may particularly be used to measure the relative abundances of substances in substance peaks eluting from upstream substance separators. Of special interest is this multi-cycle method, because the runtime of the substance separator may be shortened by at least a factor of five compared with comparable analysis methods using triple quadrupole mass spectrometers without ion mobility separators. The separation of substance ions by the ion mobility separator may even render any upstream substance separator dispensable completely, drastically shortening the duration of the analysis procedure.

The invention claimed is:

1. A mass spectrometer, comprising:
an ion source of the type being configured to continuously generate ions from a sample being supplied thereto,
a trapped ion mobility separator (TIMS) being configured to receive the generated ions in accumulated volumes thereof, and further being configured to output these accumulated volumes in short pulses of ion species that have been separated in time by their ion mobility, the trapped ion mobility separator being configured to use parallel ion accumulation (PATIMS), wherein ions are accumulated in an accumulation unit separated by their ion mobility while scanning the ions according to their ion mobility in a subsequent scanning unit, and the ions are transferred, after each scan, from the accumulation unit to the scanning unit,
a first mass filter being configured to receive the ion species and select precursor ions therefrom to be fragmented,
a fragmentation cell being configured to receive and fragment the selected precursor ions,
a second mass filter being configured to receive and select fragment ions resulting from the precursor ions by the fragmentation, and
an ion detector being configured to receive and measure an ionic output from the second mass filter.

2. The mass spectrometer according to claim 1, wherein transferring the ions from the accumulation unit to the scanning unit is configured to take place in about a millisecond.

3. The mass spectrometer according to claim 1, wherein the sample is supplied to the ion source from a substance separator.

4. The mass spectrometer according to claim 3, wherein the substance separator is one of a gas chromatograph, a liquid chromatograph, and a capillary electrophoresis device.

5. The mass spectrometer according to claim 1, comprising RF and DC voltage generators for the first and second mass filters being configured to switch the mass filters within less than a millisecond from filtering a first ion species to filtering a second ion species.

6. The mass spectrometer according to claim 5, wherein, for the switching of the first mass filter from one filtering condition to another, the RF and DC voltage generators are configured to deliver voltages which first close the mass filter, then adjust it for filtering the next ion species, and open it at the calculated and predetermined time interval of the next ion species.

7. The mass spectrometer according to claim 6, comprising DC and RF voltage generators which open and close the first mass filter by a slight increase and decrease of the DC voltage relative to the RF voltage.

8. The mass spectrometer according to claim 1, wherein the ion source is one of an electrospray ion source, chemical ionization source, photoionization source, and electron ionization source.

9. The mass spectrometer according to claim 1, wherein the first and second mass filters, $Q_1$ and $Q_3$, and the fragmentation cell, $Q_2$, constitute a triple quadrupole configuration $Q_1Q_2Q_3$.

10. A method to cyclically and quantitatively measure characteristic fragment ions of a multitude of selected precursor ions in a mass spectrometer having an ion source of the type being configured to continuously generate ions from a sample being supplied thereto, a trapped ion mobility separator (TIMS) being configured to receive the generated ions in accumulated volumes thereof, and further being configured to output these accumulated volumes in short pulses of ion species that have been separated in time by their ion mobility, a first mass filter being configured to receive the ion species and select precursor ions therefrom to be fragmented, a fragmentation cell being configured to receive and fragment the selected precursor ions, a second mass filter being configured to receive and select fragment ions resulting from the precursor ions by the fragmentation, and an ion detector being configured to receive and measure an ionic output from the second mass filter, during a single ion mobility scan of the trapped ion mobility separator (TIMS), the method comprising the steps:
  a) filling the trapped ion mobility separator (TIMS) with an accumulated volume of ions,
  b) scanning the accumulated volume of ions according to their ion mobilities, thereby generating pulses of ion species having different ion mobilities,
  c) switching the first mass filter to filter, in a calculated time interval and calculated mass range, the ions of a selected ion species appearing next during the scan, and switching the second mass filter to the calculated mass range of the characteristic fragment ion of this ion species,
  d) fragmenting the filtered ions of the selected ion species in the fragmentation cell, filtering the characteristic fragment ions in the second mass filter, and measuring the resultant ionic output with the ion detector, and
  e) repeating steps c) and d) as long as there are still selected but unmeasured ion species.

11. The method according to claim 10, wherein a stopping condition for the iteration cycles comprises one of the end of a predetermined time period, a given maximum number of measurement cycles performed, and the failure to further detect a predetermined ion species.

12. The method according to claim 11, further comprising accumulating and scanning ions in parallel in a trapped ion mobility separator with parallel ion accumulation (PATIMS), and transferring the accumulated ions, after the end of each scan, in about a millisecond from an accumulation unit to a scanning unit.

13. The method according to claim 12, wherein the trapped ion mobility separator with parallel ion accumulation (PATIMS) operates in a spatial zoom mode, accumulating and scanning ions in a preselected range of mobilities only.

14. The method according to claim 12, wherein the trapped ion mobility separator with parallel ion accumulation (PATIMS) operates in a temporal zoom mode, scanning ion mobility ranges that are expected to not contain ion species of interest very fast, and scanning selected precursor ions in preselected ranges of mobilities with low scanning speed.

15. The method according to claim 11, further comprising measuring relative abundances of substances in samples which were mixed from various probands and are tagged sample-specifically by isobaric tags with linkers cleavable at sample-specific sites, by measuring the reporter ions, stripped in the fragmentation cell from the ions thusly tagged.

16. The method according to claim 11, further comprising measuring relative abundances of substances in substance peaks eluting from upstream substance separators.

17. The method according to claim 16, wherein a runtime of the substance separator is shortened by at least a factor of five compared with comparable analysis methods with triple quadrupole mass spectrometers not being coupled to an ion mobility separator.

18. The method according to claim 10, wherein a sample to be investigated includes one of proteolytic digests of proteins extracted from biological samples, complex food/fruit/vegetable matrices to be tested for pesticides or other contaminants, and pharmaceutical drugs and their metabolites for pre-clinical studies.

19. A mass spectrometer, comprising:
  an ion source in the form of one of an electrospray ion source, chemical ionization source, photoionization source, and electron ionization source, generating ions from a sample being supplied thereto from a substance separator,
  a trapped ion mobility separator (TIMS) being configured to receive the generated ions in accumulated volumes thereof, and further being configured to output these accumulated volumes in short pulses of ion species that have been separated in time by their ion mobility, the trapped ion mobility separator being configured to use parallel ion accumulation (PATIMS), wherein ions are accumulated in an accumulation unit separated by their ion mobility while scanning the ions according to their ion mobility in a subsequent scanning unit, and the ions are transferred, after each scan, from the accumulation unit to the scanning unit,
  a first mass filter being configured to receive the ion species and select precursor ions therefrom to be fragmented,
  a fragmentation cell being configured to receive and fragment the selected precursor ions,
  a second mass filter being configured to receive and select fragment ions resulting from the precursor ions by the fragmentation, and
  an ion detector being configured to receive and measure an ionic output from the second mass filter.

20. A method to cyclically and quantitatively measure characteristic fragment ions of a multitude of selected precursor ions in a mass spectrometer having an ion source in the form of one of an electrospray ion source, chemical ionization source, photoionization source, and electron ionization source, generating ions from a sample being supplied thereto from a substance separator, a trapped ion mobility separator (TIMS) being configured to receive the generated ions in accumulated volumes thereof, and further being configured to output these accumulated volumes in short pulses of ion species that have been separated in time by their ion mobility, a first mass filter being configured to receive the ion species and select precursor ions therefrom to be fragmented, a fragmentation cell being configured to receive and fragment the selected precursor ions, a second mass filter being configured to receive and select fragment ions resulting from the precursor ions by the fragmentation, and an ion detector being configured to receive and measure an ionic output from the second mass filter, during a single ion mobility scan of the trapped ion mobility separator (TIMS), the method comprising the steps:

a) filling the trapped ion mobility separator (TIMS) with an accumulated volume of ions, b) scanning the accumulated volume of ions according to their ion mobilities, thereby generating pulses of ion species having different ion mobilities, c) switching the first mass filter to filter, in a calculated time interval and calculated mass range, the ions of a selected ion species appearing next during the scan, and switching the second mass filter to the calculated mass range of the characteristic fragment ion of this ion species, d) fragmenting the filtered ions of the selected ion species in the fragmentation cell, filtering the characteristic fragment ions in the second mass filter, and measuring the resultant ionic output with the ion detector, and e) repeating steps c) and d) as long as there are still selected but unmeasured ion species.

* * * * *